(12) United States Patent
Temelli et al.

(10) Patent No.: US 8,939,969 B2
(45) Date of Patent: Jan. 27, 2015

(54) ELECTROSURGICAL DEVICE WITH OFFSET CONDUCTIVE ELEMENT

(75) Inventors: Deniz Temelli, London (CA); Neil Godara, Milton (CA)

(73) Assignee: Kimberly-Clark, Inc., Mississauga, Ontario (CA)

( * ) Notice: Subject to any disclaimer, the term of this patent is extended or adjusted under 35 U.S.C. 154(b) by 627 days.

(21) Appl. No.: 13/249,908

(22) Filed: Sep. 30, 2011

(65) Prior Publication Data

US 2013/0085487 A1 Apr. 4, 2013

(51) Int. Cl.
*A61B 18/18* (2006.01)
*A61B 18/14* (2006.01)
*A61B 18/00* (2006.01)

(52) U.S. Cl.
CPC ......... *A61B 18/1477* (2013.01); *A61B 18/1482* (2013.01); *A61B 2018/00178* (2013.01); *A61B 2018/00339* (2013.01); *A61B 2018/00434* (2013.01); *A61B 2018/00005* (2013.01); *A61B 2018/00589* (2013.01); *A61B 2018/00821* (2013.01)
USPC .................................. 606/41; 606/45; 606/49

(58) Field of Classification Search
CPC .............................................. A61B 2018/1405
USPC ................................................ 606/41, 45, 49
See application file for complete search history.

(56) References Cited

U.S. PATENT DOCUMENTS

| | | | |
|---|---|---|---|
| 5,571,147 A | 11/1996 | Sluijter et al. | |
| 6,146,380 A * | 11/2000 | Racz et al. | 606/41 |
| 6,607,529 B1 | 8/2003 | Jones et al. | |
| 6,736,835 B2 | 5/2004 | Pellegrino et al. | |
| 7,306,596 B2 | 12/2007 | Hillier et al. | |
| 7,593,778 B2 | 9/2009 | Chandran et al. | |
| 7,962,223 B2 | 6/2011 | Young et al. | |
| 8,177,784 B2 | 5/2012 | Van Wyk et al. | |
| 8,211,104 B2 | 7/2012 | Mccullagh et al. | |
| 2010/0185082 A1 | 7/2010 | Chandran et al. | |
| 2011/0077644 A1 | 3/2011 | Pham et al. | |

FOREIGN PATENT DOCUMENTS

WO    WO 01/45579    6/2001

OTHER PUBLICATIONS

Radiofrequency Nitinol Probe & Radiofrequency Generator Connector Cable Instructinos for Use, Mar. 9, 2011—6 pages.
International Search Report for PCT/CA2012/050591; Nov. 26, 2012.

* cited by examiner

*Primary Examiner* — Michael Kahelin
*Assistant Examiner* — Mallika D Fairchild
(74) *Attorney, Agent, or Firm* — Dority & Manning, P.A.

(57) ABSTRACT

A device for forming a lesion includes a hub defining a passageway and a shaft attached to the hub and defining a lumen. The shaft has a proximal end and a distal end extending away from the hub. The shaft includes an electrically conductive material on at least a portion of an inner surface and on at least a portion on an outer surface. A conductive member has a longitudinal axis and is attached to a mounting structure mateable with mounting structure of the hub so that the conductive member extends through the passageway into the lumen so that at least near the hub the conductive member longitudinal axis is spaced from the lumen longitudinal axis to create electrical contact between the conductive member outer surface and the shaft inner surface.

22 Claims, 5 Drawing Sheets

ELECTROSURGICAL DEVICE WITH OFFSET CONDUCTIVE ELEMENT

TECHNICAL FIELD

The present invention relates to a medical device for applying energy, particularly radio frequency electrical energy, to a patient's body.

BACKGROUND

Chronic back pain is a cause for concern throughout the world and especially in the United States, affecting as many as 80% of all Americans at some point in their lives. Lower back pain can arise from any number of sources, including but not limited to conditions of the spinal vertebrae themselves, the intervertebral disks and the facet joints of the spine. Although the precise cause of back pain is still a matter of debate, it is recognized that nerves present in these structures contribute to the sensation and transmission of these pain signals. Some of the recent advances in the treatment of back pain, therefore, have focused on treating the nerves deemed to be contributing to the pain sensations.

A minimally invasive technique of delivering high frequency electrical current has been shown to relieve localized pain in many patients. The high frequency electrical current is typically delivered from a generator via one or more electrodes that are placed in a patient's body. Resistance to the high frequency electrical current at the tip of the electrode causes heating of adjacent tissue and when the temperature increases sufficiently, the tissue coagulates. The temperature that is sufficient to coagulate unmyelinated nerve structures is 45° C., at which point a lesion is formed and pain signals are blocked. This procedure is known as tissue denervation and it usually results in significant pain relief. Radio frequency (RF) denervation refers to tissue denervation using energy in the RF range. This technique has proven especially beneficial in the treatment of back pain and more specifically, lower back pain.

U.S. Pat. No. 6,736,835 B2, issued May 18, 2004, U.S. Pat. No. 5,571,147, issued Nov. 5, 1996 and PCT patent application WO 01/45579 A1, published Jun. 28, 2001, amongst others, disclose methods and devices for performing RF denervation of various tissues of the back, including spinal vertebrae, intervertebral disks and facet joints of the spine. In general, the procedure entails introduction of an electrosurgical device into the body, positioning the device proximate to the neural tissue to be treated and applying RF electrical energy in order to denervate the tissue.

More specifically, an electrosurgical device comprising a cannula having a hollow shaft and a removable stylet therein is inserted into a patient's body and positioned at a desired treatment site. The cannula typically comprises an elongate, insulated region, along with an electrically conductive and exposed distal tip. Once the distal tip of the cannula is in position, the stylet is withdrawn and the distal end of a probe capable of delivering high frequency electrical energy is inserted until the distal end of the probe is at least flush with the exposed distal tip of the cannula. The proximal end of the probe is connected to a signal generator capable of generating high frequency electrical current. Once the distal end of the probe is in position, energy is supplied by the generator via the probe to denervate the tissue proximate to the distal end of the probe.

If the probe and cannula do not make good electrical contact along their lengths, then the RF energy dissipation can be undesirably uneven along the probe. Hot spots can occur and energy may not be fully or evenly transmitted to the tip region as desired. In situations where the probe portion within the cannula is substantially thinner than the cannula, this lack of or periodic contact can be accentuated further.

Accordingly, there is a continued need for improvement in systems used for RF treatment of bodily tissue, and it would be beneficial to have a device and a system that is improved and/or overcomes some or all of the limitations of the prior art.

SUMMARY

According to certain aspects of the present disclosure, a device for forming a lesion includes a hub defining a passageway therethrough and having a mounting structure at one end of the passageway and a shaft attached to the hub and defining lumen therethrough having a longitudinal axis. The shaft has a proximal end attached to the hub in communication with the passageway and a distal end extending away from the hub. The shaft includes an electrically conductive material on at least a portion of an inner surface and an electrically conductive material on at least a portion on an outer surface. A conductive member has a longitudinal axis and is attached to a mounting structure mateable with the mounting structure of the hub so that the conductive member extends through the passageway into the lumen so that at least near the hub the conductive member longitudinal axis is spaced from the lumen longitudinal axis, thereby assisting in creating electrical contact between the conductive member outer surface and the shaft inner surface. Various options and modifications are possible.

For example, the shaft and/or the conductive member may be flexible along at least a part of its length. The conductive member may be selectively removable from the lumen, and the shaft may be part of or may include a cannula. The shaft defining the lumen may have a gauge size and the conductive member may have a gauge size that is smaller than the gauge size of the lumen.

The conductive member may be connectable to a radio frequency generator and may include a hypotube. An obturator may be provided that is removably insertable into the lumen for substantially filling the lumen when the shaft is inserted into a surgical site. The obturator may have an outer diameter that is less than a diameter of the shaft inner surface. The conductive member may extend from the lumen when fully inserted.

According to certain other aspects of the disclosure, a device is disclosed for forming a lesion and is insertable into a hub defining a passageway therethrough and having a mounting structure at one end of the passageway. A shaft is attached to the hub and defines a lumen therethrough having a longitudinal axis and having a proximal end being attached to the hub in communication with the passageway. The shaft has a distal end extending away from the hub and includes an electrically conductive material on at least a portion of an inner surface and an electrically conductive material on at least a portion on an outer surface. The device itself includes a conductive member having a longitudinal axis. The conductive member is attached to a mounting structure mateable with the mounting structure of the hub so that the conductive member extends through the passageway into the lumen so that at least near the hub the conductive member longitudinal axis is spaced from the lumen longitudinal axis, thereby assisting in creating electrical contact between the conductive member outer surface and the shaft inner surface. As above, various options and modifications are possible.

These features and others will become apparent in the detailed description that follows.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
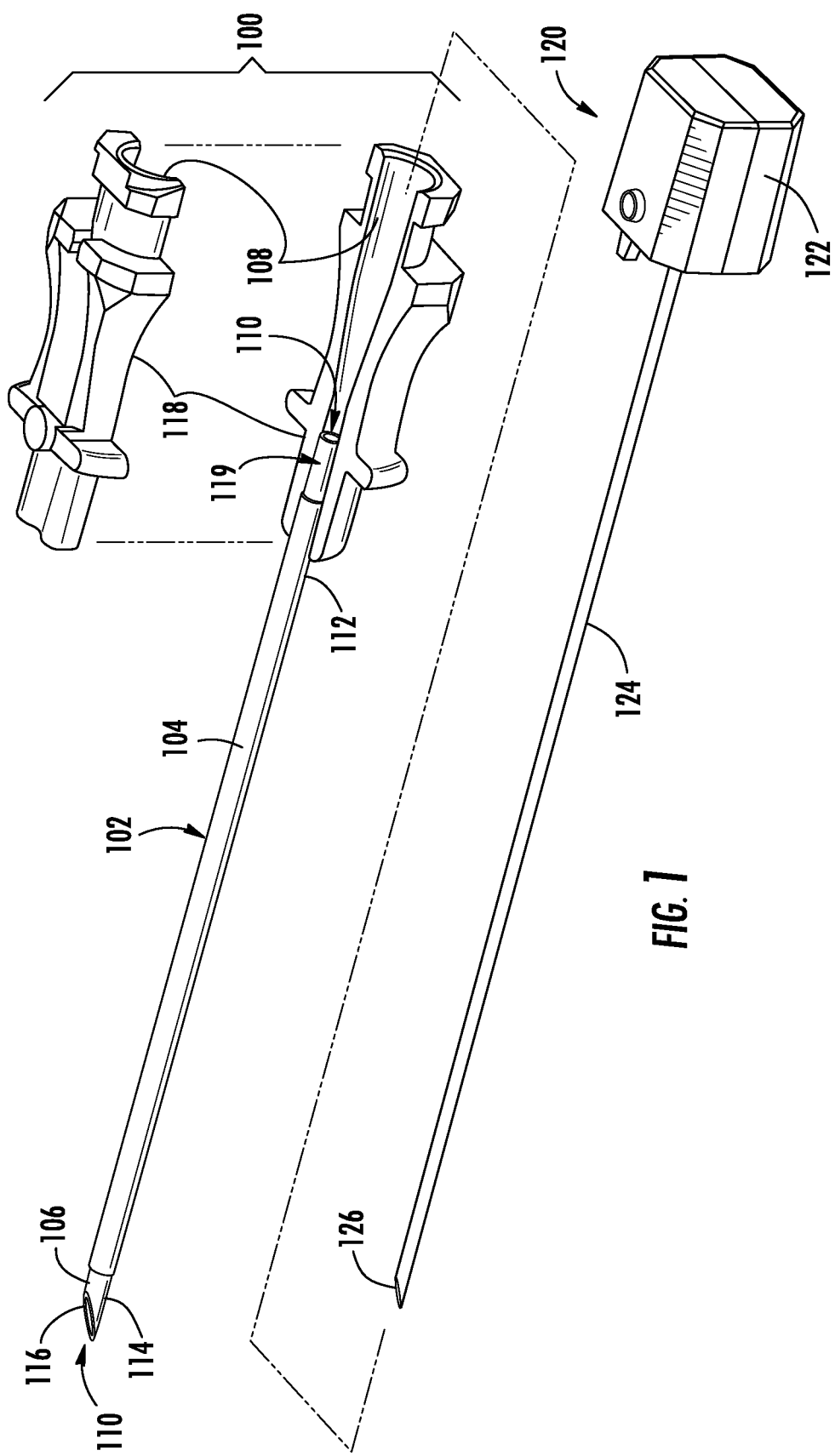
FIG. 1 is an exploded perspective view of a cannula and a stylet.

With specific reference now to the drawings in detail, the particulars shown are by way of example and for purposes of illustrative discussion of some embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, proximal generally indicates that portion of a device or system next to or nearer to a user (when the device is in use), while the term distal generally indicates a portion further away from the user (when the device is in use).

Figure 2:
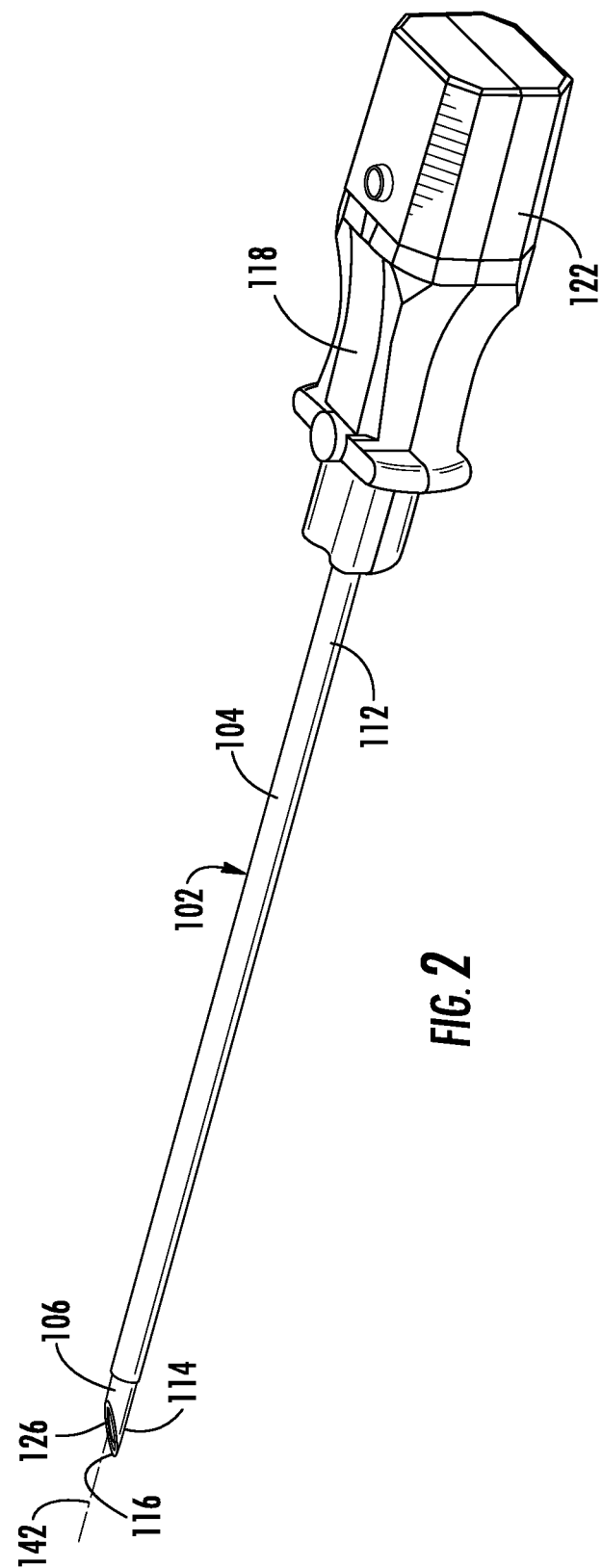
FIG. 2 is a perspective view of the cannula and stylet of FIG. 1 assembled together.

FIG. 1 shows an exploded perspective view of a cannula 100 with a related stylet 120, while FIG. 2 illustrates a perspective view of cannula 100 with stylet 120 inserted. Optionally, cannula 100 is manufactured from an electrically conductive and radiopaque material, and a shaft 102 of cannula 100 is at least partially coated with an electrically insulating material 104. Suitable materials for electrically insulating material 104 include, but are not limited to, parylene and PTFE. A distal tip portion 106 of shaft 102 remains exposed and electrically conductive. Due to the conductive nature of distal tip portion 106, the distal tip portion may be described as an active electrode or active tip. Distal tip portion 106 is optionally sharp to facilitate penetration into a patient's body. Alternatively, distal tip portion 106 may be blunt, rounded, straight, beveled, rigidly bent, or may take on other forms depending on the particular application. Radiopaque elements, dots, bands, markers, etc. (not shown) may be optionally positioned on shaft 102 so as to assist in visualizing the position of shaft 102 under X-ray fluoroscopic imaging.

Shaft 102 defines a lumen 110 extending longitudinally from a proximal region 112 to a distal region 114 of cannula 100. In this first embodiment, distal tip portion 106 of the shaft defines an aperture 116 in communication with lumen 110 of shaft 102. The combination of lumen 110 and aperture 116 allows for the introduction of a fluid or other material into a patient's body.

Cannula 100 optionally further comprises a hub 118 located at or adjacent to proximal region 112. Hub 118 is optionally manufactured from ABS (Acrylonitrile Butadiene Styrene) or a similar material and may be attached to shaft 102 at inner area 119 using various methods, including but not limited to insert molding, gluing and other forms of bonding. As shown in FIG. 1, hub 118 is in two pieces, although hub could be formed from a single piece.

In the context of the present disclosure, the term hub indicates a fitting or any other means of facilitating a secure connection between separate components such as a cannula and a probe. As such, hub 118 is optionally structured to cooperatively engage and mate with a probe, stylet, conductive member, or other device which may be introduced into shaft 102 via an opening 108. Opening 108 defines a passageway through hub 118, part of which is filled by shaft 102. Lumen 110 of shaft 102 may be optionally sized to simultaneously accommodate a stylet, probe, conductive member or other device as well as a diagnostic or therapeutic agent. The diagnostic or therapeutic agents may include, but are not limited to, contrast or other chemical agents, pharmaceuticals, and biological agents. In other embodiments, lumen 110 may be designed to receive a probe, stylet, conductive member or other device without having sufficient space to accommodate a diagnostic or therapeutic agent. In such embodiments, the probe, stylet, conductive member or other device may be removed from lumen 110, allowing for injection of a diagnostic or therapeutic agent if so desired. It should be noted that, while cannula 100 has been described as having a single lumen, alternate embodiments with more than one lumen are also envisioned. Likewise, although this embodiment depicts a cannula with a single aperture, more than one aperture may be disposed along the cannula and the one or more apertures may be disposed at various locations along cannula 100 and are not limited to the locations shown in the appended drawings.

Stylet 120 may be inserted into lumen 110 of shaft 102. In this embodiment, stylet 120 is adapted to assist in piercing a patient's skin and tissue for entry to a treatment area. As is known in the art, inserting a stylet (functioning as an obturator) into a cannula prior to insertion of the cannula into a patient's body helps to ensure that no tissue is forced into a lumen of the cannula by occluding any apertures in the cannula shaft. Stylet 120 optionally comprises a cap 122 adapted to cooperatively engage and mate with hub 118 of cannula 100 and a stylet shaft 124 extending from the cap. Optionally, stylet shaft 124 has a pointed tip 126, which may be a trocar, conical, bevel, or other shape to allow for easy penetration of tissue when cannula 100 and stylet 120 are introduced into the patient's body. The shape of tip 126 and tip portion 106 may be complementary. As above, a radiopaque element (not shown) may optionally be located somewhere on stylet shaft 124 to help distinguish the position of the shaft under fluoroscopy.

Figure 3:
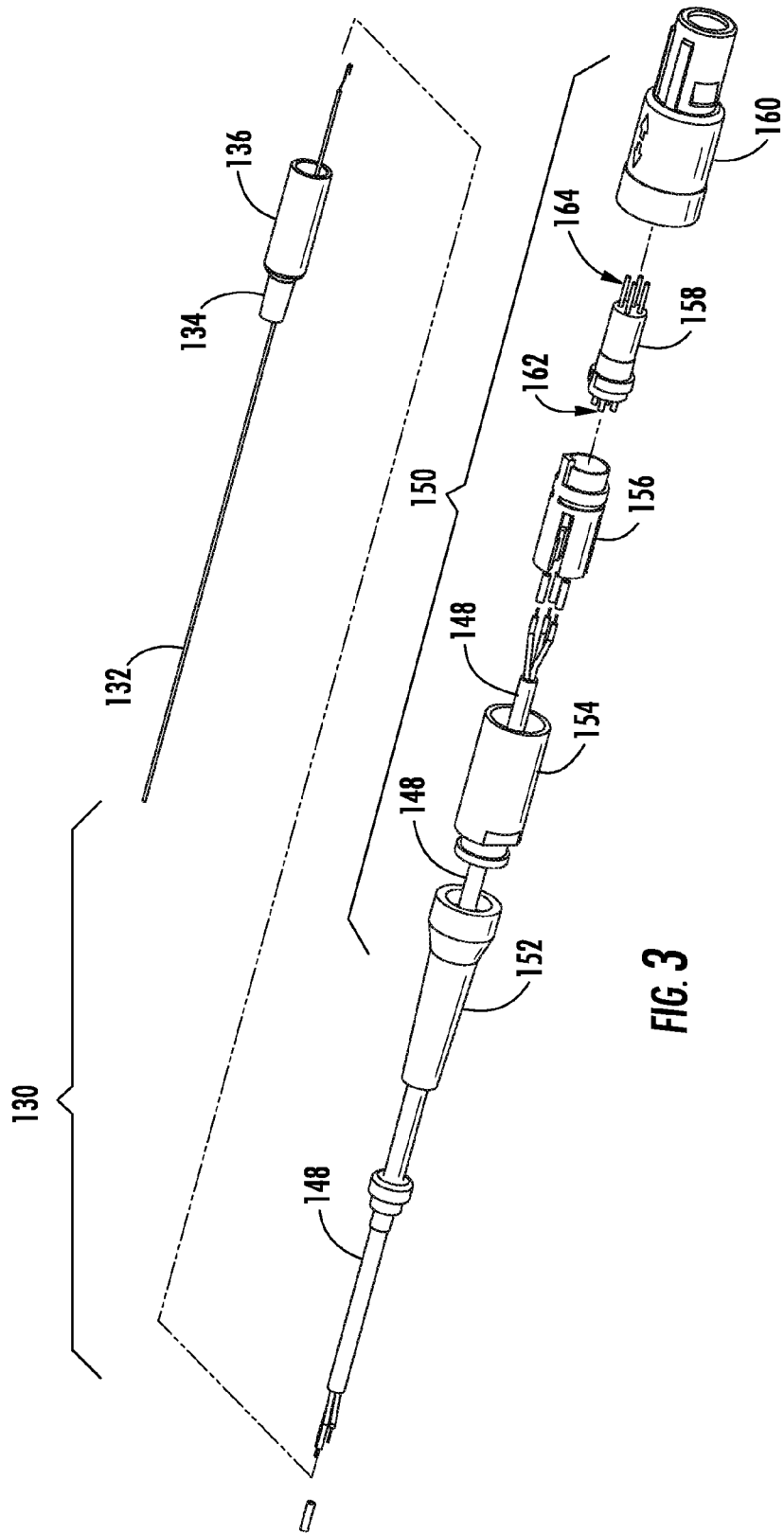
FIG. 3 an exploded perspective view of an RF probe assembly.
Figure 4:
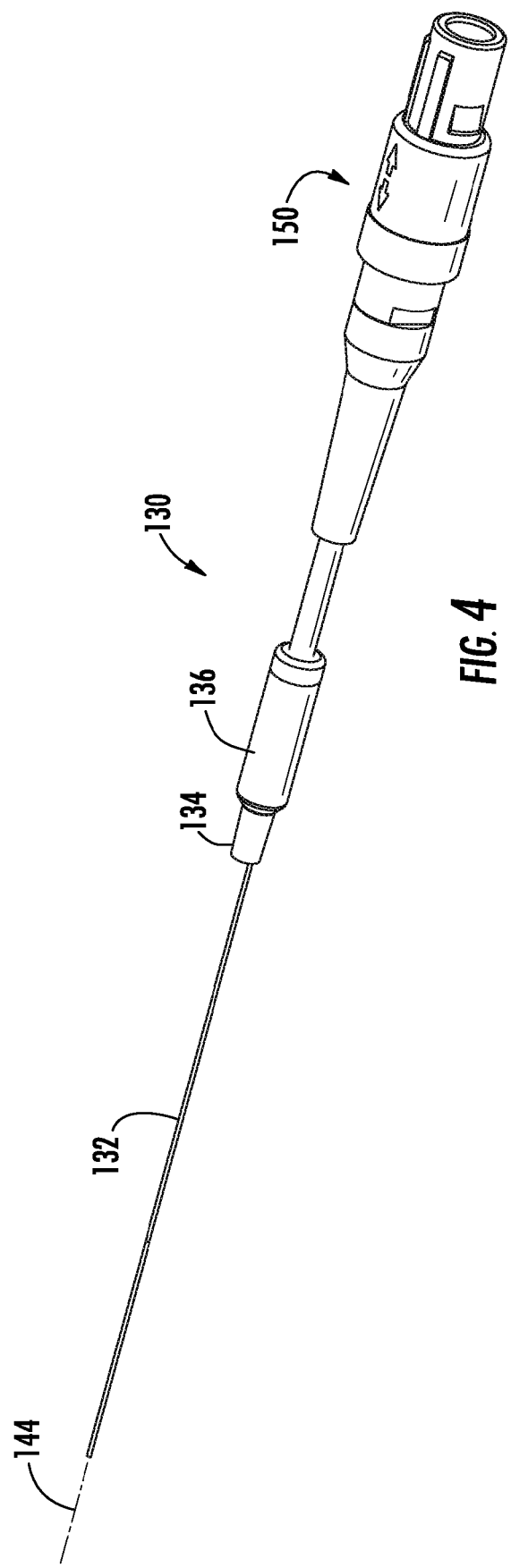
FIG. 4 is perspective view of the RF probe assembly of FIG. 3.

RF probe assembly 130 is shown in FIGS. 3 and 4. Assembly 130 is just one of many possible electrosurgical devices that could be employed according to the present disclosure.

Thus, the present invention is not limited to the disclosed device, or RF devices in general.

As shown, RF probe assembly 130 includes a conductive member 132 attached to a mounting structure 134 mateable with the mounting structure (proximal end of opening 108) of hub 118. Conductive member 132 may comprise a hypotube, and may include various wiring connections, a thermocouple, internal cooling, etc. as is conventional. For example, conductive member may comprise an RF Nitinol Probe, available from Kimberly-Clark, Inc. Such probe may be used with disposable cannulas also available from Kimberly-Clark, Inc. The probes and cannulas are available in different gauges and lengths. For example, the cannulas may have a gauge of 16-22, and may be straight or curved, and conductive member should be sized to fit within the cannula gauge selected. Alternatively, a cannula gauge may be selected in view of the intended use, conductive member gauge, other elements to be used with the cannula, etc.

Figure 6:
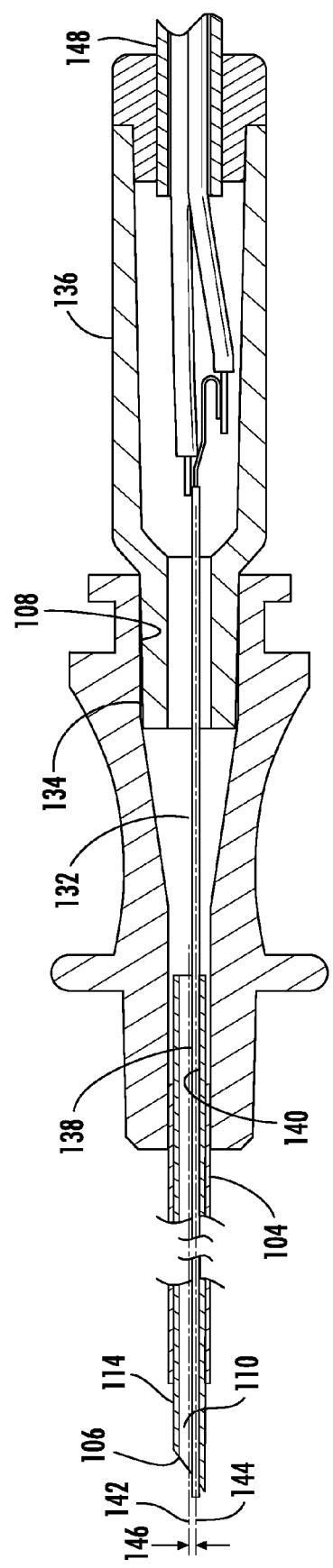
FIG. 6 is a partial sectional view as in FIG. 5, with the probe assembly as in FIG. 3 connected to a cannula as in FIG. 1.

Mounting structure 134 may comprise, as shown, the distal end of a handle portion 136 of probe assembly 130. When handle portion 136 is inserted into hub 118 as shown in FIG. 6, conductive member 132 extends into and through lumen 110. At least part of the outer surface 138 of conductive member 132 that extends into lumen 110 is conductive, as is at least part of the inner surface 140 of the lumen.

Lumen 110 defined by shaft 106 has a longitudinal axis 142 and conductive member 132 has a longitudinal axis 144. These axes 142,144 are aligned, with reference to the mating structures 108,134, so that the axes are longitudinally spaced from each other by an amount 146 when handle 136 is attached to hub 118. If desired, interacting elements such as grooves and ridges, etc., (not shown) could be provided on mating structures 108,134 to dictate one or more predetermined orientations upon attachment. Shaft 102 and/or conductive member 132 may be relatively flexible (as opposed to rigid) so that some bending is possible during insertion and use. Such bending may improve contact between the elements.

As shown in FIG. 6, contact between lumen inner surface 140 and conductive member outer surface 138 is enhanced by virtue of the offset 146. Accordingly, electrical connection between the proximal end 112 and distal end of 114 lumen 110 and conductive member 132 is substantially more continuous than without the offset. Energy flow and dissipation is normalized, relatively hotter and cooler spots are reduced or avoided.

Figure 5:
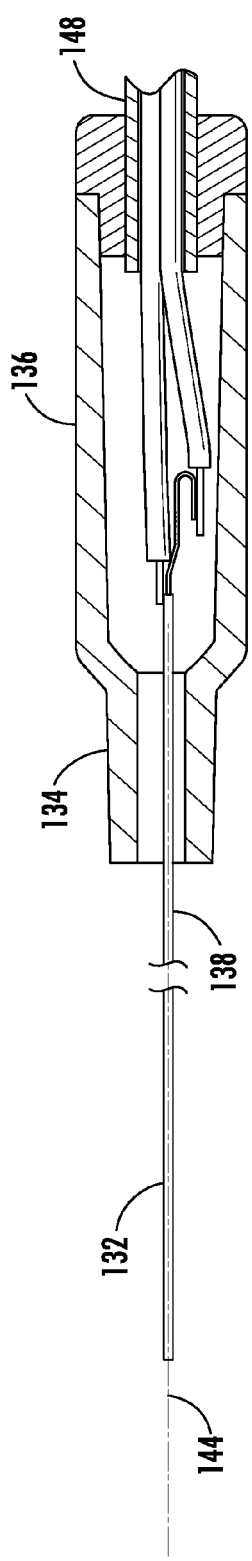
FIG. 5 is partial sectional of a portion of the RF probe assembly of FIG. 3 showing an offset conductive member.

As shown in FIG. 5, one way to achieve such offset axes is to form handle mating structure 134 and conductive member 132 with an offset, and to form the cannula mating structure 108 and lumen with no offset, relative to a central axis. However, such offset location could be reversed. Or both sides could be offset in some way, whether equally or unequally. Accordingly, the present invention includes any such arrangement of parts whereby when a conductive member is inserted into a lumen, there is a central axis offset. The amount of offset possible and desired would of course depend on the gauges of the lumen within the cannula and the conductive member (and the differences therein), whether other elements were to extend into the lumen in a desired application, whether the shaft defining the lumen were curved or straight, etc.

In order to achieve the offset, the conductive member gauge could be chosen to be smaller than that of the lumen defined by the shaft within the cannula. For example, if conductive member were sized one gauge size smaller than the lumen within the shaft, a certain amount of offset would be possible. If selected to be two, three four, five, six, etc. gauge sizes smaller, then greater offset would be possible. The mating structures 134,108 would be adjusted accordingly in view of the gauge size difference to achieve the desired contact between conductive member and cannula. However, it a difference in gauge size is not needed in all aspects of the invention.

Other elements of probe assembly 130 may include a probe cable 148 connecting to conductive member 132 inside of handle 136. Cable 148 may carry electrical wiring for applying energy (RF or otherwise), cooling elements, thermocouple connections, etc., depending on the desired application. As shown, a three conductor cable is provided with attachments for RF energy and a thermocouple. Main handle portion 150 includes a bend relief section 152, a backnut 154, a collet connector 156, an electrical connector portion 158, and a handle base 160. Leads from cable 148 extend through the handle portion and connect to distal elements 162 on connector portion 158. Proximal elements 164 connect with a connector (not shown) on a cable used to connect handle portion 150 to an energy source, such as an RF generator such as that available from Kimberly-Clark, Inc. and formerly known as a Baylis Pain Management Generator. However, it should be understood that the above description of the probe assembly components is but one example and many types of probes for delivering energy, whether RF or other energy, could be used according to the invention. Thus, no limitation should be understood to be intended from the example described above.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

We claim:

1. A device for forming a lesion comprising:
   a hub defining a passageway therethrough and having a mounting structure at one end of the passageway;
   a shaft attached to the hub and defining lumen therethrough having a longitudinal axis, the shaft having a proximal end attached to the hub in communication with the passageway and a distal end extending away from the hub, the shaft including an electrically conductive material on at least a portion of an inner surface and an electrically conductive material on at least a portion of an outer surface; and
   a conductive member having a longitudinal axis, the conductive member being attached to a mounting structure mateable with the mounting structure of the hub so that the conductive member extends through the passageway into the lumen, wherein the conductive member longitudinal axis is spaced apart from the lumen longitudinal axis by an offset, thereby assisting in creating electrical contact between the conductive member outer surface and the shaft inner surface.

2. The device of claim 1, wherein the shaft is flexible along at least a part of its length.

3. The device of claim 1, wherein the conductive member is flexible along at least a part of its length.

4. The device of claim 1, wherein the conductive member is selectively removable from the lumen.

5. The device of claim 1, wherein the shaft defining the lumen comprises a cannula.

6. The device of claim 1, wherein the conductive member is connectable to a radio frequency generator.

7. The device of claim 6, wherein the conductive member includes a hypotube.

8. The device of claim 1, further including an obturator removably insertable into the lumen for substantially filling the lumen when the shaft is inserted into a surgical site.

9. The device of claim 8, wherein the obturator has an outer diameter that is less than a diameter of the shaft inner surface.

10. The device of claim 1, wherein the conductive member extends from the lumen when fully inserted.

11. The device of claim 1, wherein the shaft defining the lumen has a gauge size and the conductive member has a gauge size that is smaller than the gauge size of the lumen.

12. A device for forming a lesion insertable into a hub defining a passageway therethrough and having a mounting structure at one end of the passageway, a shaft attached to the hub and defining a lumen therethrough having a longitudinal axis and having a proximal end being attached to the hub in communication with the passageway, the shaft having a distal end extending away from the hub, the shaft including an electrically conductive material on at least a portion of an inner surface and an electrically conductive material on at least a portion on an outer surface, the device comprising:

a conductive member having a longitudinal axis, the conductive member being attached to a mounting structure mateable with the mounting structure of the hub so that the conductive member extends through the passageway into the, wherein the conductive member longitudinal axis is spaced apart from the lumen longitudinal axis by an offset, thereby assisting in creating electrical contact between the conductive member outer surface and the shaft inner surface.

13. The device of claim 12, wherein the shaft is flexible along at least a part of its length.

14. The device of claim 12, wherein the conductive member is flexible along at least a part of its length.

15. The device of claim 12, wherein the conductive member is selectively removable from the lumen.

16. The device of claim 12, wherein the shaft defining the lumen comprises a cannula.

17. The device of claim 12, wherein the conductive member is connectable to a radio frequency generator.

18. The device of claim 17, wherein the conductive member includes a hypotube.

19. The device of claim 12, further including an obturator removably insertable into the lumen for substantially filling the lumen when the shaft is inserted into a surgical site.

20. The device of claim 19, wherein the obturator has an outer diameter that is less than a diameter of the shaft inner surface.

21. The device of claim 12, wherein the conductive member extends from the lumen when fully inserted.

22. The device of claim 12, wherein the shaft defining the lumen has a gauge size and the conductive member has a gauge size that is smaller than the gauge size of the lumen.

* * * * *